(12) United States Patent
Danino (10) Patent No.: US 10,799,342 B2
(45) Date of Patent: Oct. 13, 2020

(54) TREATMENT OF TRICUSPID INSUFFICIENCY

(71) Applicant: Innoventric Ltd., Rehovot (IL)

(72) Inventor: Amir Danino, Rehovot (IL)

(73) Assignee: Innoventric Ltd., Rehovot (IL)

( * ) Notice: Subject to any disclaimer, the term of this patent is extended or adjusted under 35 U.S.C. 154(b) by 0 days.

(21) Appl. No.: 15/721,120

(22) Filed: Sep. 29, 2017

(65) Prior Publication Data

US 2018/0021130 A1 Jan. 25, 2018

Related U.S. Application Data

(63) Continuation of application No. PCT/IB2017/050534, filed on Feb. 1, 2017.

(60) Provisional application No. 62/292,422, filed on Feb. 8, 2016.

(51) Int. Cl.
| | |
|---|---|
| *A61F 2/24* | (2006.01) |
| *A61F 2/07* | (2013.01) |
| *A61F 2/06* | (2013.01) |
| *A61F 2/856* | (2013.01) |

(52) U.S. Cl.
CPC ............. *A61F 2/2412* (2013.01); *A61F 2/07* (2013.01); *A61F 2/2418* (2013.01); *A61F 2/856* (2013.01); *A61F 2002/061* (2013.01); *A61F 2002/068* (2013.01); *A61F 2230/0004* (2013.01); *A61F 2230/0006* (2013.01); *A61F 2230/0008* (2013.01); *A61F 2230/0019* (2013.01); *A61F 2230/0023* (2013.01); *A61F 2230/0069* (2013.01); *A61F 2250/001* (2013.01); *A61F 2250/0098* (2013.01)

(58) Field of Classification Search
CPC ..................................................... A61B 17/08
See application file for complete search history.

(56) References Cited

U.S. PATENT DOCUMENTS

| | | | |
|---|---|---|---|
| 5,957,978 A | * | 9/1999 | Blom ................ A61M 16/0468 |
| | | | 128/200.26 |
| 7,799,072 B2 | | 9/2010 | Greenberg |
| 8,470,013 B2 | | 6/2013 | Duggal et al. |
| 8,636,789 B2 | | 1/2014 | Ivancev et al. |
| 8,870,944 B2 | | 10/2014 | Sochman et al. |
| 2004/0093070 A1 | | 5/2004 | Hojeibane et al. |
| 2004/0106976 A1 | | 6/2004 | Bailey et al. |
| 2005/0059923 A1 | | 3/2005 | Gamboa |
| 2005/0060026 A1 | | 3/2005 | Gamboa |

(Continued)

FOREIGN PATENT DOCUMENTS

| | | |
|---|---|---|
| EP | 2522306 A1 | 11/2012 |
| WO | WO 2004/093935 A2 | 11/2004 |
| WO | 2016008526 A1 | 1/2016 |

OTHER PUBLICATIONS

International Search Report for International Application PCT/IB2017/05034, dated Jun. 12, 2017.

(Continued)

*Primary Examiner* — Yashita Sharma
(74) *Attorney, Agent, or Firm* — Cooley LLP (57) ABSTRACT

A tricuspid insufficiency treatment device includes a vena cava member (12) implantable in a vena cava of a patient. The vena cava member (12) is formed with a fenestration (14) and further includes a blocking member (16) arranged to block and unblock the fenestration (14).

21 Claims, 4 Drawing Sheets

(56) References Cited

U.S. PATENT DOCUMENTS

| | | | |
|---|---|---|---|
| 2006/0276813 A1 | 12/2006 | Greenberg | |
| 2006/0287712 A1* | 12/2006 | Eidenschink | A61F 2/856 623/1.35 |
| 2007/0156233 A1 | 7/2007 | Kapadia et al. | |
| 2007/0203572 A1 | 8/2007 | Heuser et al. | |
| 2007/0250154 A1* | 10/2007 | Greenberg | A61F 2/07 623/1.35 |
| 2008/0114446 A1* | 5/2008 | Hartley | A61F 2/07 623/1.13 |
| 2008/0161901 A1 | 7/2008 | Heuser et al. | |
| 2010/0106240 A1* | 4/2010 | Duggal | A61B 17/12022 623/1.15 |
| 2015/0230916 A1* | 8/2015 | Ivancev | A61F 2/07 623/1.13 |
| 2015/0282958 A1 | 10/2015 | Centola et al. | |
| 2017/0165061 A1 | 6/2017 | Figulla et al. | |
| 2017/0239043 A1 | 8/2017 | Wei | |

OTHER PUBLICATIONS

European Examination Report issued for Application Serial No. EP 17709795.3, dated Jan. 21, 2019.
Response to the European Examination Report dated May 30, 2019, for Application Serial No. EP 17709795.3.
Written Opinion issued for International Application PCT/IB2017/050534, dated Aug. 14, 2018.
International Preliminary Report on Patentability issued for International Application PCT/IB2017/050534, dated Aug. 14, 2018.
Communication issued for European Application Serial No. EP 17709795.3, dated Dec. 11, 2019.

* cited by examiner

TREATMENT OF TRICUSPID INSUFFICIENCY

This application is a continuation of the PCT/IB2017/050534, filed Feb. 1, 2017, which claims the benefit of priority to U.S. Provisional Application No. 62/292,422, filed Feb. 8, 2016 the contents of each are herein incorporated by reference in their entireties.

FIELD OF THE INVENTION

The present invention generally relates to medical devices for implantation in the heart, and particularly, but not only, to a stent based device for treating an incompetent or regurgitant tricuspid (atrioventricular) valve.

BACKGROUND OF THE INVENTION

The tricuspid valve prevents back flow of blood from the right ventricle into the right atrium when it closes during ventricular systole and allows blood to flow from right atrium into right ventricle when it opens during ventricular diastole.

An incompetent tricuspid valve causing tricuspid regurgitation (TR) may occur from tricuspid annular dilation and right ventricular enlargement. TR is often secondary to left heart failure from myocardial or valvular causes, right ventricular volume or pressure overload and dilation of cardiac chambers. TR causes right atrial overload that is transmitted to the superior and inferior vena cava (SVC, IVC) and their tributaries. Eventually, this leads to hepatic congestion, ascites, anasarca, peripheral edema and other clinical symptoms of congestive heart failure. If untreated, significant tricuspid regurgitation frequently leads to heart failure and death.

Clinically available treatments for TR are open heart surgery or medication. However, open heart surgery for the replacement/repair of the tricuspid valve is rarely carried out, mainly due to its high mortality and morbidity rates. Medication, on the other hand, does not solve the problem and allows the disease to progress, leaving the patients with a deteriorated quality of life and cardiac function.

Due to the high surgical risk of tricuspid valve replacement/repair, currently, the vast majority of TR patients are deemed inoperable. This results in an extremely large number of untreated patients with significant TR.

SUMMARY OF THE INVENTION

The present invention seeks to a stent based device for treating an incompetent or regurgitant tricuspid valve, as described in more detail hereinbelow. Unlike the prior art, the present invention does not attempt to mimic the structure of the tricuspid valve, rather the present invention provides a blocking member to selectively unblock or block flow into or out of the right atrium.

The device is intended for the functional replacement of a regurgitant tricuspid valve, while avoiding the complex anatomy of the right ventricle and atrioventricular valve. Although not restricted for percutaneous implantations, the device can improve the transcatheter functional replacement of the tricuspid valve. The invention treats the regurgitant tricuspid valve without having to deal with the complex anatomy of the tricuspid valve. The invention obviates the need for complex imaging modalities. Implantation of the device of the invention involves a simple deployment of a single stent structure.

The device is a stent graft with a valved wall. The stent graft extends from the superior vena cava to the inferior vena cava (or vice versa) and may be anchored to the tubular structure of the vena cava using the stent radial force or any other anchoring means, such as sutures, barbs, diverging stent graft ends or elements inserted into the SVC/IVC tributary vessels (such as, but not limited to, the hepatic and azygos veins). The portion of the device which is in the right atrium (between the SVC and IVC) has one or more apertures in the graft material and one or more blocking members which cover the apertures and selectively prevent flow through them. Depending on the pressure gradient across the blocking members, the blocking members can either open (such as by being pushed away from the apertures by inner pressure directed through the apertures) to allow flow from within the stent graft towards its outer environment, or can close (such as by being pushed towards the apertures by outer pressure directed towards the device) to prevent the fluid backflow from the outer device environment towards its inner lumen.

For example, in the suggested position of the vena cava and right atrium, the device is typically subjected to pressure gradients that open the blocking members during diastole, when the venous pressure is higher than the ventricular and atrial pressure, and to oppositely directed pressure gradients during ventricular systole when the ventricular and atrial pressures (both chambers being at similar pressures due to the incompetent native tricuspid valve) are higher than the venous pressure. Thus, in this anatomical position, the blocking members are open to allow forward blood flow during diastole and are closed to prevent back flow of blood during ventricular systole. In this anatomical position the device acts as a second valve above the native tricuspid valve which is left untouched.

The stent element in the stent graft may be a self-expandable material such as medical grade shape memory alloys or polymers, it can also be a balloon expandable material such as a medical grade metal alloy or polymer. The stent structure may be a woven or braided mesh, it may be independent or interconnected stent wires with the typical M or Z shape, and it may also be laser cut from a tube.

The graft material is a flow barrier that significantly restricts the passage of body fluids (e.g. blood) through it. The graft material may be a fabric, either braided or woven, it may be a polymer either braided, woven, injected or immersed, and it may also be a biological material either from human or animal source. With time, in the body, the graft material may become covered with tissue, this tissue itself may function as a flow barrier.

Connecting of the stent and graft material may be done using sutures, adhesives, embedding of the stent material within the graft material, and passing of the stent material through the graft material.

Although the device is not restricted to percutaneous methods of delivery, transcatheter is the preferred method of delivery into the relevant anatomy. It is noted that in the closed state of the blocking members, the device is generally tubular and has no element protruding outwards or inwards from the stent graft body. This construction is advantageous for transcatheter delivery, because the simple shape of a tube can be easily mounted in, and deployed out of, a catheter. When deployed out of a catheter, the blocking members respond to the pressure gradient and start performing as a valve. This structure allows for sheathing and un-sheathing of the device with no device preparation or constraints. There is no need for additional stent bodies that are off-axis or parallel to the device tubular axis, which can hinder the straight-forward sheathing or deployment of the device.

It is contemplated that the device may be useful in other applications other than tricuspid insufficiency, such as but not limited to, treating mitral regurgitation, for example.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1A:
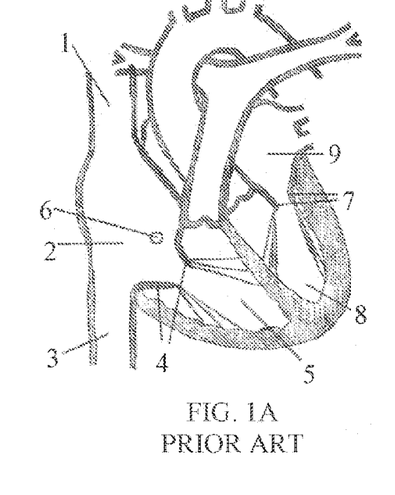
FIGS. 1A and 1B are simplified illustrations of a heart at diastole and ventricular systole, respectively, wherein during ventricular systole, the tricuspid valve is not properly closed, such that there is tricuspid regurgitation.
Figure 1B:
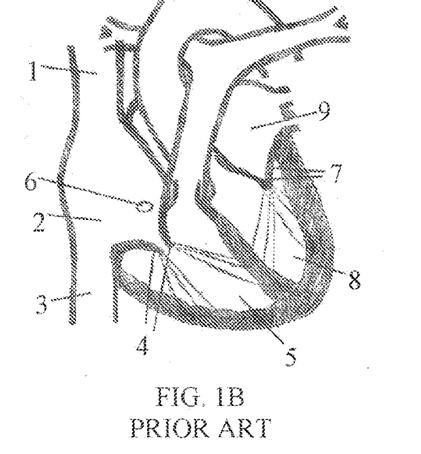

First a brief description of the heart anatomy is presented with reference to FIGS. 1A and 1B. The superior vena cava 1 returns blood from the upper half of the body, and opens into the upper and back part of the right atrium 2 via a valve-less orifice which is directed downward and forward. The inferior vena cava 3, typically larger than the superior, returns blood from the lower half of the body, and opens into the lowest part of the atrium 2, near the atrial septum. Its orifice is directed upward and backward, and protected by the inferior vena cava valve (called the Eustachian valve). The tricuspid valve 4 is located between the right atrium 2 and the right ventricle 5.

The coronary sinus 6 opens into the right atrium 2, between the orifice of the inferior vena cava and the atrio-ventricular opening. It returns blood from the substance of the heart and is protected by a semicircular valve, the valve of the coronary sinus (also called the valve of Thebesius). The mitral valve 7 is between the left ventricle 8 and the left atrium 9.

Ventricular systole induces increased pressure in the right and left ventricles 5 and 8. Pressure in the ventricles rises to a level above that of the atria 2 and 9, thus closing the tricuspid and mitral valves 4 and 7. FIG. 1B shows that the tricuspid valve 4 is not properly closed, such that there is tricuspid regurgitation.

Figure 3A:
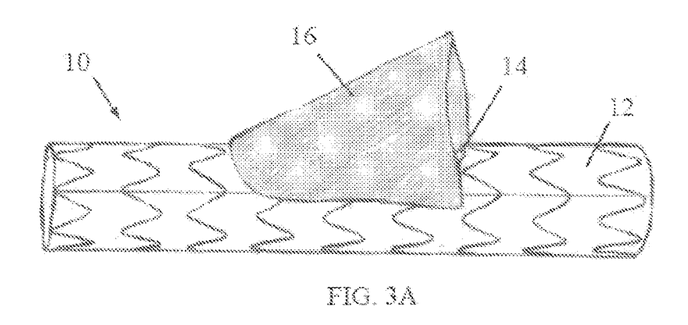
FIGS. 3A and 3B are simplified illustrations of a tricuspid insufficiency treatment device, constructed and operative in accordance with a non-limiting embodiment of the present invention, with a flap valve in blocked and unblocked positions, respectively (alternatively FIGS. 3A and 3B illustrate two different embodiments, wherein in FIG. 3A the flap valve is normally open and in FIG. 3B the flap valve is normally closed)

Reference is now made to FIG. 3A, which illustrates a tricuspid insufficiency treatment device 10, in accordance with a non-limiting embodiment of the present invention, for correcting the problem of tricuspid regurgitation.

Tricuspid insufficiency treatment device 10 includes a vena cava member 12 implantable in the superior vena cava (SVC) or inferior vena cava (IVC). The side wall of vena cava member 12 is formed with a right atrium aperture 14 (also referred to as a fenestration 14) and also includes a blocking member 16 arranged to block and unblock the right atrium aperture 14. For example, the blocking member 16 may be a flap valve, in which blocking member 16 is a flap or cover pivoted to a portion of vena cava member 12. The blocking member can open outwards away from the side wall of the vena cava member, or in other embodiments, can open sideways or other directions.

The blocking member 16 can be normally open (FIG. 3A) or normally closed (FIG. 3B) with respect to the one or more apertures 14. The mechanism of a normally open or closed blocking member can be of further assistance in controlling the degree of the device regurgitation or stenosis, respectively. For example, a normally open blocking member requires a certain measurable and controlled closing force. Thus, a normally open blocking member can create a measurable and controlled level of regurgitation. Conversely, a normally closed blocking member can create a measurable and controlled level of stenosis.

Figure 3B:
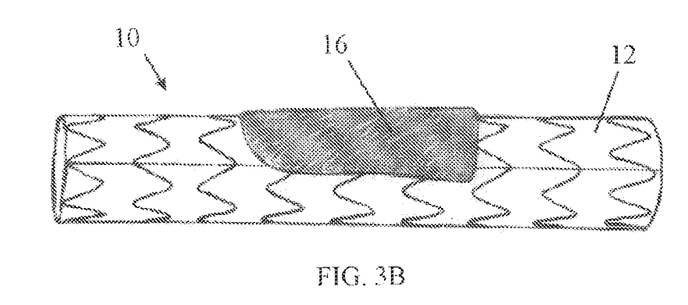

The device can be implanted so that the right atrium aperture 14 is aligned with (faces in a direction of) the orifice of the SVC or with the orifice of the IVC or it can face in other directions, such as sideways (anteriorly/posteriorly). Thus, the blocking member 16 may have its open portion (right atrium aperture 14) directed towards the superior, inferior, anterior or posterior part of the right atrium.

Figure 5:
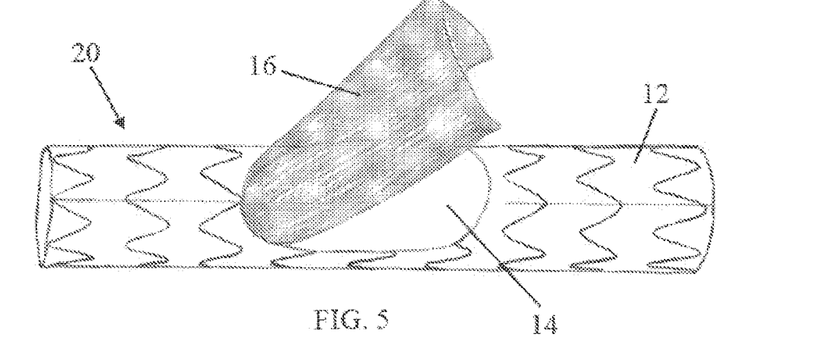
FIG. 5 is a simplified illustration of a tricuspid insufficiency treatment device, constructed and operative in accordance with another non-limiting embodiment of the present invention, with the flap valve being connected to the stent graft using a relatively small portion of its perimeter.
Figure 6:
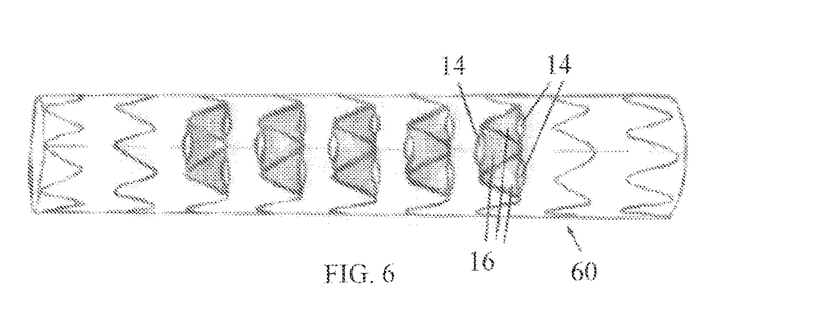
FIG. 6 is a simplified illustration of a tricuspid insufficiency treatment device, constructed and operative in accordance with another non-limiting embodiment of the present invention, with more than one aperture and blocking member.
Figure 7:
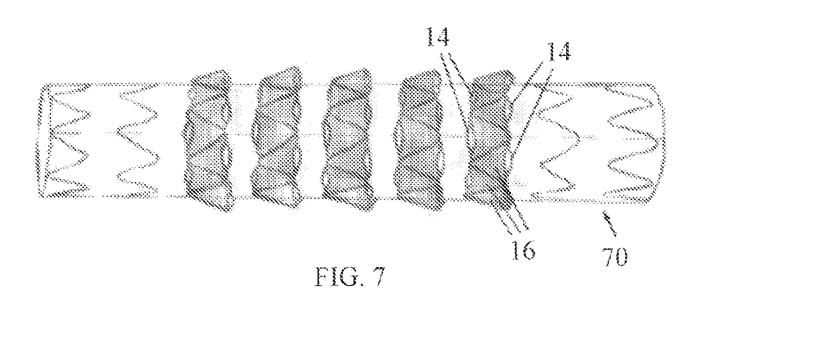
FIG. 7 is a simplified illustration of a tricuspid insufficiency treatment device, constructed and operative in accordance with another non-limiting embodiment of the present invention, including multiple fenestrations and blocking members all around (or almost all around) the stent graft perimeter.

In FIGS. 3A-3B and 5, one right atrium aperture 14 and one blocking member 16 are provided; in FIGS. 6 and 7, more than one right atrium aperture 14 is provided, each one with its blocking member 16. The vena cava member 12 may be a stent graft, which can be self-expanding (e.g., shape memory alloy, polymer and the like) or balloon expandable (e.g., steel alloys, polymers and the like). The blocking member 16 may be made from the same graft material as the vena cava member or from other graft materials. It may be free of, or include, reinforcing structure, such as wires, rods, tubes, sutures or a mesh. The stent graft and blocking members may be immersed, sprayed or covered by anti-coagulant agents, anti-platelet agents, tissue growth accelerating or inhibiting agents, antibiotics, statins, anti-inflammatory agents and other materials or medications. The stent structure may include, without limitation, stent rings, independent or interconnected, a braided or laser-cut mesh, a braided or laser cut tubular structure and others. The device 10 may be fixed in-situ, for example, by the radial force of the expandable members, barbs, diverging vena cava member ends, stent or other members deployed in the tributaries, or other suitable means. Any subsequent tissue growth on the device may also help in fixation.

The blocking member 16 may be connected to the vena cava member 12 by any suitable means, such as but not limited to, sutures, adhesives, polymer embedding, welding, ultrasonic welding, a unified graft and blocking member material, and others.

The vena cava member 12 may be generally cylindrical, but alternatively may be non-cylindrical. The term "cylindrical" as used throughout the specification and claims includes not only a circular cross-section, but also elliptical and other curved cross-sections. The diameter of vena cava member 12 may be uniform over its axial length. Alternatively, the diameter of vena cava member 12 may vary over its axial length. The blocking member 16 may have a triangular shape with rounded corners as shown. Alternatively, it may have an oval, rectangular, circular or other shape.

Figure 2:
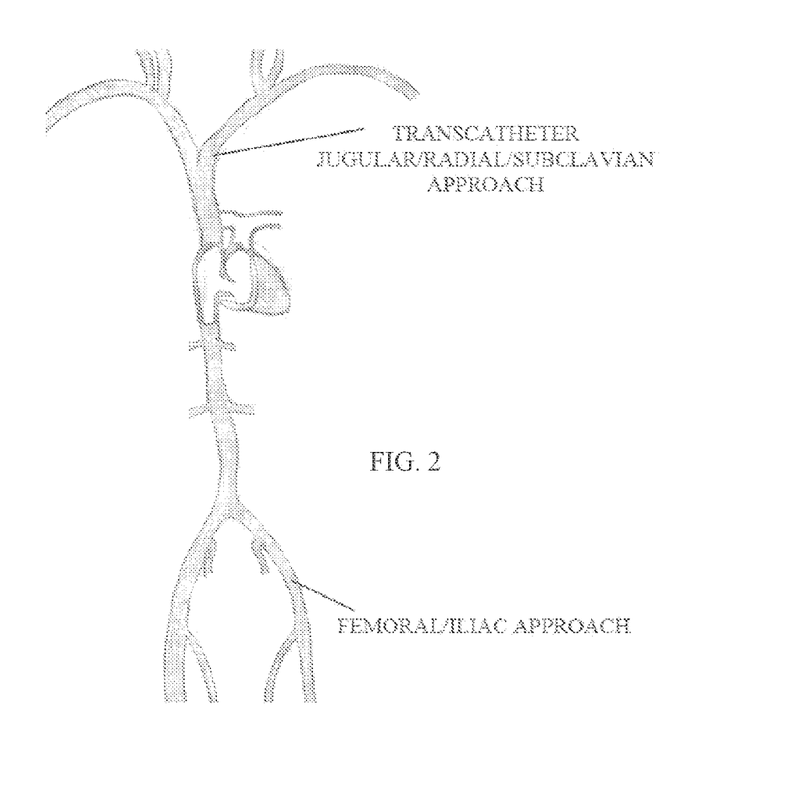
FIG. 2 is a simplified illustration of a percutaneous venous path for implantation of the device of the invention, either from lower or upper extremities.

The device may be delivered percutaneously or by surgical means. For example, the device may be delivered percutaneously through the IVC in a transcatheter femoral/iliac approach (FIG. 2), or through the SVC in a transcatheter jugular/radial/subclavian approach (FIG. 2).

Radio-opaque markers may be provided on the device for axial and rotational positioning within the body lumen. Typically, radio-opaque markers can be in the shape of the letters 'L', 'E' or 'C' to mark the rotational position of the device, these or other markers can be placed on various axial positions on the device, so that the implanting operator can understand and control the device axial position.

Figure 4A:
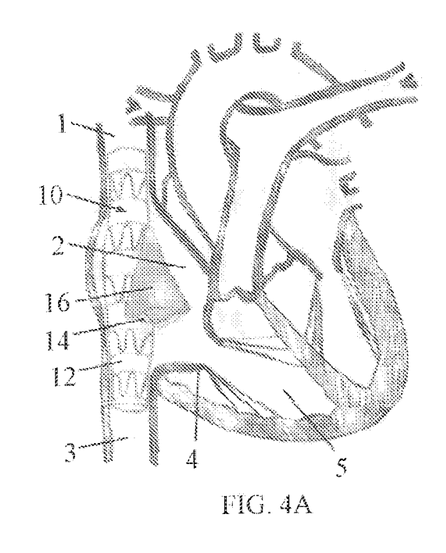
FIGS. 4A and 4B are simplified illustrations of the tricuspid insufficiency treatment device implanted in the vasculature, respectively in diastole and systole.
Figure 4B:
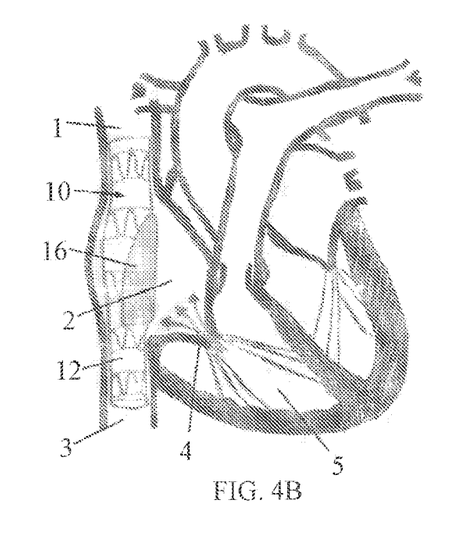

Reference is now made to FIGS. 4A and 4B, which illustrate the tricuspid insufficiency treatment device 10 implanted in the vasculature. FIG. 4A shows diastole, in which the pressure in the right ventricle 5 drops (e.g., to 0 mm Hg) and the blood pressure in the vena cava causes the blocking member 16 to open and allow flow through the right atrium aperture 14.

Systole is shown in FIG. 4B, in which the pressure in the right ventricle 5 increases. The inadequate tricuspid valve 4 does not completely prevent back flow of blood from the right ventricle 5 into the right atrium 2 because it cannot close completely. The systole pressure causes the blocking member 16 to close and prevent flow through the right atrium aperture 14 (blocked from view in FIG. 4B). This helps diminish back flow of blood from the right ventricle and atrium into the venous system. As seen in FIG. 4B, when blocking member 16 blocks fenestration 14, the tubular vena cava member and the blocking member together have a closed cylindrical outer shape. This structure is advantageous for sheathing and un-sheathing the device in a delivery catheter.

Reference is now made to FIG. 5 which illustrates a tricuspid insufficiency treatment device 50, constructed and operative in accordance with another non-limiting embodiment of the present invention. Device 50 includes a blocking member 56 connected to a vena cava member (stent graft) 52 in a relatively small portion of its perimeter, thus enabling large volume flow with relatively low resistance in every diastole. During ventricular systole, the blocking member 56 fully impedes back flow of blood as in other device embodiments.

Reference is now made to FIG. 6, which illustrates a tricuspid insufficiency treatment device 60, constructed and operative in accordance with another non-limiting embodiment of the present invention. Device 60 includes more than one blocking member 16 and more than one fenestration 14. Some of the blocking members 16 face in the same directions and others face in different directions.

The embodiment of FIG. 6, with its multiple fenestrations 14 and blocking members 16 may provide improved hemodynamics, with a very small chance of valve clogging and insufficient blood supply. It may reduce turbulence, and diminish no-flow areas and other insufficient blood flows that could occur with a single opening. In addition, the device deployment is less sensitive to axial position of the flap valves (fenestrations 14 and blocking members 16) since there are many of them.

The embodiment of FIG. 6 enables performing future interventions with access to reach anywhere in the right atrium. For example, some of the flap valves retain their function even during interventions such as puncturing of the fossa ovalis, implanting a pace maker or defibrillator or other procedures. Even if the procedure interferes with the function of some of the flap valves, the rest (majority) of the flap valves maintain their function for the benefit of the interventional procedure and the patient.

In case of tissue growth, thrombi or other causes of device deterioration, the multiple flap valves significantly improve the chances of an efficient and safe blood flow.

In this and any other embodiment of the invention, each fenestration 14 can have one dedicated blocking member 16 or several blocking members 16, and the blocking members 16 can either cover the entire fenestration 14 or a portion thereof.

Reference is now made to FIG. 7, which illustrates a tricuspid insufficiency treatment device 70, constructed and operative in accordance with another non-limiting embodiment of the present invention, including multiple fenestrations 14 circumferentially all around (or partially around) the vena cava member 12. This embodiment eliminates any need for a specific rotational orientation of the device.

Figure 8:
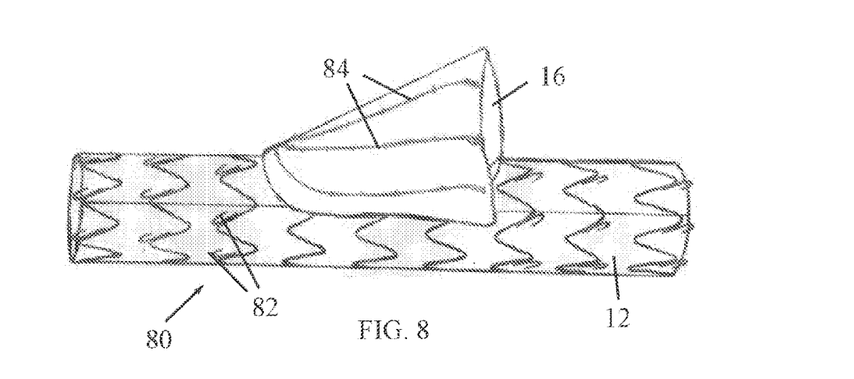
FIG. 8 is a simplified illustration of a tricuspid insufficiency treatment device, constructed and operative in accordance with another non-limiting embodiment of the present invention, including barbs on the vena cava member and reinforcing struts on the blocking member.

Reference is now made to FIG. 8, which illustrates a tricuspid insufficiency treatment device 80, constructed and operative in accordance with another non-limiting embodiment of the present invention. Device 80 includes barbs 82 on the vena cava member 12, which may assist in anchoring the device at the implantation site. Device 80 may also include reinforcing structure such as struts 84 on the blocking member (or members) 16, which may increase the strength of the blocking member (or members) 16 against the flow impinging on it (or them).

Figure 9:
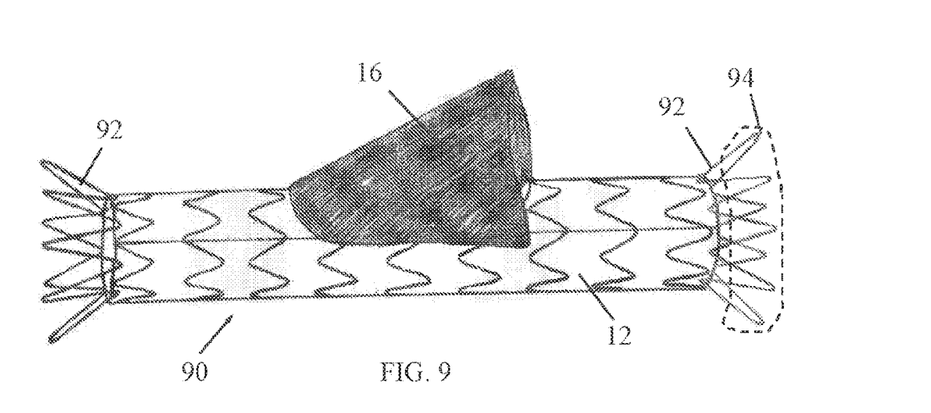
FIG. 9 is a simplified illustration of a tricuspid insufficiency treatment device, constructed and operative in accordance with another non-limiting embodiment of the present invention, with diverging stent graft ends, which may be covered, partially covered or not covered by graft material.

Reference is now made to FIG. 9, which illustrates a tricuspid insufficiency treatment device 90, constructed and operative in accordance with another non-limiting embodiment of the present invention. Device 90 includes diverging stent graft ends 92, which may be covered, partially covered or not covered by graft material 94 (shown partially in the figure in broken lines). The diverging stent graft ends 92 may assist in anchoring the device at the implantation site.

Accordingly, the tricuspid insufficiency treatment device 10 provides benefits for a patient suffering from tricuspid regurgitation. The device may be implanted surgically and percutaneously (e.g. via femoral, jugular, or subclavian approach).

The tricuspid insufficiency treatment device 10 has a smooth tubular shape when in the closed condition. This has the advantage of easy installation of the device into a catheter and deployment to site at the heart, and even provides the possibility of re-sheathing the device into the catheter during the procedure.

What is claimed is:

1. A tricuspid insufficiency treatment apparatus comprising:
   a cylindrical, tubular member having a tubular axis and configured for implantation within a vena cava of a patient, the tubular member formed with a sidewall having an exterior surface; and
   at least one blood-flow valve comprising:
      a fenestration formed in the sidewall of the tubular member; and
      a blocking member arranged to open outwardly from the exterior surface so as to block and unblock the flow of blood out through the fenestration during ventricular systole and ventricular diastole, respectively.

2. The apparatus of claim 1, wherein the at least one blood-flow valve comprises a plurality of blood-flow valves, each blood-flow valve of the plurality of blood-flow valves comprising:
   a fenestration formed in the sidewall, and
   a blocking member arranged to block and unblock a respective fenestration.

3. The apparatus of claim 2, wherein the plurality of blood-flow valves are arranged circumferentially along the sidewall.

4. The apparatus of claim 2, wherein each blocking member comprises a flap or cover pivotally attached at or proximate a portion of a respective fenestration and arranged to block and unblock the fenestration during ventricular systole and ventricular diastole, respectively, such that the fenestration is unblocked in a direction opposite to the attachment of the flap or cover.

5. The apparatus according to claim 2, wherein at least one of the blood-flow valves of the plurality of blood-flow valves is arranged toward the first end of the tubular member and at least one of the blood-flow valves of the plurality of blood-flow valves is arranged toward the second end of the tubular member.

6. The apparatus of claim 1, wherein the tubular member and the blocking member of the blood-flow valve form a closed cylindrical outer shape when the blocking member blocks the fenestration.

7. The apparatus of claim 2, wherein the tubular member and the plurality of blocking members of the plurality of blood-flow valves form a closed cylindrical outer shape when the blocking members block the fenestrations.

8. The apparatus of claim 2, wherein some of the blocking members are arranged to unblock respective fenestrations in a first direction and some of the blocking members are arranged to unblock their respective fenestrations in a second direction.

9. The apparatus according to claim 2, wherein the tubular member comprises an expandable stent body.

10. The apparatus of claim 2, wherein some of the blocking members are arranged to unblock respective fenestrations during ventricular diastole in a direction of an orifice of the superior vena cava of the patient.

11. The apparatus of claim 2, wherein some of the blocking members are arranged to unblock respective fenestrations during ventricular diastole in a direction of an orifice of the inferior vena cava of the patient.

12. The apparatus of claim 2, wherein each of the plurality of blocking members each comprise a reinforcing structure.

13. The apparatus of claim 2, wherein the plurality of blood-flow valves comprise at least one first set of blood-flow valves arranged toward the first end of the tubular member and at least one second set of blood-flow valves arranged toward the second end of the tubular member.

14. A tricuspid insufficiency treatment apparatus comprising:
   a tubular member configured for implantation within a vena cava of a patient, the tubular member formed with a sidewall having an exterior surface; and
   a plurality of blood-flow valves arranged circumferentially along the sidewall, each comprising:
      a fenestration formed in the sidewall; and
      a blocking member arranged to open outwardly from the exterior surface so as to block and unblock the flow of blood out through the fenestration during ventricular systole and ventricular diastole, respectively,
   wherein each blocking member comprises a flap or cover pivotally attached at or proximate a portion of a respective fenestration and arranged to block and unblock the fenestration, such that the fenestration is unblocked in a direction opposite to the attachment of the flap or cover.

15. The apparatus of claim 14, wherein some of the blocking members are arranged to unblock respective fenestrations in a first direction and some of the blocking members are arranged to unblock their respective fenestrations in a second direction.

16. The apparatus of claim 14, wherein some of the blocking members are arranged to unblock respective fenestrations during ventricular diastole in a direction of an orifice of the superior vena cava of the patient.

17. The apparatus of claim 14, wherein some of the blocking members are arranged to unblock respective fenestrations during ventricular diastole in a direction of an orifice of the inferior vena cava of the patient.

18. The apparatus of claim 14, wherein the plurality of blood-flow valves comprise at least one first set of blood flow valves arranged toward the first end of the tubular member and at least one second set of blood flow valves arranged toward the second end of the tubular member.

19. A tricuspid insufficiency treatment apparatus comprising:
   a tubular member configured for implantation within a vena cava of a patient, the tubular member formed with a sidewall having an exterior surface; and
   a plurality of blood-flow valves arranged circumferentially along the sidewall, each comprising:
      a fenestration formed in the sidewall; and
      a blocking member arranged to open outwardly from the exterior surface so as to block and unblock the flow of blood out through the fenestration during ventricular systole and ventricular diastole, respectively,
   wherein:
      each blocking member comprises a flap or cover pivotally attached at or proximate a portion of a respective fenestration and arranged to block and unblock the fenestration, such that the fenestration is unblocked in a direction opposite to the attachment of the flap or cover, and
      the tubular member and the plurality of blocking members of the plurality of blood-flow valves form a closed cylindrical outer shape when the blocking members block the fenestrations during ventricular systole.

20. The apparatus of claim 1, wherein the blocking member comprises a flap or cover pivotally attached to a respective fenestration.

21. A tricuspid insufficiency treatment apparatus comprising:
- a tubular member configured for implantation within a vena cava of a patient, the tubular member formed with a sidewall having an exterior surface; and
- a plurality of blood-flow valves arranged circumferentially along the sidewall, each comprising:
  - a fenestration formed in the sidewall; and
  - a blocking member arranged to open outwardly from the exterior surface so as to block and unblock the flow of blood out through the fenestration during ventricular systole and ventricular diastole, respectively.

* * * * *